United States Patent [19]

Trinh et al.

[11] Patent Number: 6,077,318
[45] Date of Patent: *Jun. 20, 2000

[54] METHOD OF USING A COMPOSITION FOR REDUCING MALODOR IMPRESSION

[75] Inventors: Toan Trinh, Maineville; Jerome Paul Cappel, Cincinnati; Philip Anthony Geis, West Chester; Judith Ann Hollingshead, Batavia; Mark Lee McCarty, Loveland; Susan Schmaedecke Zwerdling, Wyoming, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/898,215

[22] Filed: Jul. 22, 1997

Related U.S. Application Data

[63] Continuation of application No. 08/617,949, Mar. 13, 1996, Pat. No. 5,670,475, which is a continuation of application No. 08/289,731, Aug. 12, 1994, abandoned.

[51] Int. Cl.[7] .................. C11D 3/50; A61L 9/01
[52] U.S. Cl. .............. 8/137; 510/470; 510/101; 510/405; 510/462; 510/102; 510/103; 510/104; 510/406; 510/407; 510/109; 510/191; 510/194; 510/195; 510/214; 510/276; 252/8.91; 424/76.1; 424/65; 424/43; 424/76.5; 424/76.6; 424/76.7
[58] Field of Search ................... 510/470, 101, 510/405, 462, 102, 103, 104, 406, 407, 109, 191, 194, 195, 214, 276; 252/8.91; 424/76.1, 65, 43, 76.2, 45, 76.5, 76.6, 76.7; 239/1; 8/115.6, 137; 512/1, 3; 134/42

[56] References Cited

U.S. PATENT DOCUMENTS

| D. 244,991 | 7/1977 | Weckman et al. | D9/63 |
|---|---|---|---|
| D. 275,078 | 8/1984 | Wassergord et al. | D9/300 |

(List continued on next page.)

FOREIGN PATENT DOCUMENTS

| 0 132 038 A1 | 1/1985 | European Pat. Off. . | |
|---|---|---|---|
| 0 386 714 A2 | 9/1990 | European Pat. Off. . | |
| 0 032 779 A2 | 7/1991 | European Pat. Off. . | |
| 4008919-A1 | 9/1991 | Germany . | |
| 53-41440 | 4/1978 | Japan | A61K 7/32 |
| 58-124452 | 7/1983 | Japan | A61L 9/01 |
| 61-128973 | 6/1986 | Japan | A61L 9/01 |
| 63-164953 | 7/1988 | Japan . | |
| 1-256597 | 10/1989 | Japan . | |
| 02-174847 | 7/1990 | Japan . | |
| 2174847 | 7/1990 | Japan . | |
| 3-170415 | 7/1991 | Japan | A61K 7/32 |
| 3-284616 | 12/1991 | Japan | A61K 7/16 |
| 618699 | 12/1948 | United Kingdom . | |
| 941105 | 11/1963 | United Kingdom . | |
| 1458836 | 12/1976 | United Kingdom . | |
| 89/02698 | 4/1989 | WIPO | A01K 1/015 |
| WO 90/14849 | 12/1990 | WIPO . | |
| 91/12029 | 8/1991 | WIPO | A61L 9/01 |
| WO 95/15186 | 6/1995 | WIPO . | |

OTHER PUBLICATIONS

Derwent Abstract 37653A/21 for JP 5–3041,440, Apr. 1978.
Derwent Abstract 89–344274/47 for JP 1–256,596, Oct. 1989.
Derwent Abstract 90–346225/46 for JP 2–251,681, Oct. 1990.
Derwent Abstract 91–262298/36 for JP 3–170,415, Jul. 1991.
"Semio Activity of Flavor and Gragrance Molecules on Various Insect Species", B. D. Mookherjee, et al., *Bioactive Volatile Compounds from Plants*, 1993 ACS Symposium Series, pp. 35–48 (Month Unknown).
Formation of Inclusion Complex between Cyclodextrin and d–Limonese by a Twin Screw Kneader, T. Furuta, et al., Department of Biotechnology Tottori University (Date Unknown).
Effects of Water and Alcohol and the formation of Inclusion complexes of D–Limonene and cyclodextrins, T. Furuta, et al., *Supramolecular Chemistry*, vol. 1, pp. 321–325 (1993). (Month Unknown).
Studies on the Industrial Production and Application of Cyclodextrins, *Denpun Kagaku*, vol. 36, No. 1, pp. 35–42 (1989). (Month Unknown).
Application of Cyclodextrins to Foods, Toiletries and Other Products in Japan, H. Hashimoto, Ensuiko Sugar Refining Co. (Date Unknown).
Interaction between Preservatives and 2–Hydroxypropyl–β–Cylodextrin, T. Loftsson, et al., *Drug Development and Industrial Pharmacy*, 18(18), 1477–1484, (1992) (Month Unknown).
H. Bennett (ed.), *The Chemical Formulary*, vol. 1, pp. 148–151 (New York 1933) (month unknown).
Mary Ellen Pinkham & Dale Burg, *Mary Ellen's Clean House!*, pp. 132–137, 166–169 ( New York 1993) (month unknown).

*Primary Examiner*—Alan Diamond
*Attorney, Agent, or Firm*—Jason J. Camp; Robert B. Aylor

[57] ABSTRACT

The present invention relates to an aqueous composition for reducing malodor impression. The composition comprises from about 0.01% to about 1%, by weight of the composition, of perfume wherein the perfume preferably comprises ingredients having a Clog P of 3 or smaller. Optionally, but preferably, the composition comprises from about 0.1% to about 5%, by weight of the composition of, water-soluble cyclodextrin, from about 0.1% to about 10%, by weight of the composition, of water-soluble metallic salt, from about 0% to about 3%, by weight of the composition, of solubilizing aid. The composition is essentially free of any material that would soil or stain fabric and contains less than about 5%, by weight of the composition of low molecular weight monohydric alcohols.

41 Claims, No Drawings

U.S. PATENT DOCUMENTS

| | | |
|---|---|---|
| D. 277,978 | 3/1985 | Bundschuh ............................. D23/17 |
| 2,422,145 | 6/1947 | Taylor . |
| 2,544,093 | 3/1951 | Kilgore . |
| 2,893,958 | 7/1959 | Phillips . |
| 3,074,891 | 1/1963 | Kulka . |
| 3,172,817 | 3/1965 | Leupold et al. . |
| 3,426,011 | 2/1969 | Parmerter et al. . |
| 3,436,776 | 4/1969 | Davis . |
| 3,453,257 | 7/1969 | Parmerter et al. . |
| 3,453,258 | 7/1969 | Parmerter et al. . |
| 3,453,259 | 7/1969 | Parmerter et al. . |
| 3,453,260 | 7/1969 | Parmerter et al. . |
| 3,459,731 | 8/1969 | Gramera et al. . |
| 3,553,191 | 1/1971 | Parmerter et al. . |
| 3,565,887 | 2/1971 | Parmerter et al. . |
| 3,600,325 | 8/1971 | Kaufman et al. . |
| 3,674,688 | 7/1972 | Schwartz et al. . |
| 3,872,604 | 3/1975 | Keller . |
| 3,965,014 | 6/1976 | Giordano et al. ........................ 510/517 |
| 4,082,223 | 4/1978 | Nozawa . |
| 4,161,288 | 7/1979 | McKinney . |
| 4,184,985 | 1/1980 | Scheuermann et al. . |
| 4,265,899 | 5/1981 | Lewis et al. . |
| 4,267,166 | 5/1981 | Yajima . |
| 4,272,385 | 6/1981 | Crete et al. ............................ 252/608 |
| 4,274,560 | 6/1981 | Cater . |
| 4,299,737 | 11/1981 | Meffert et al. . |
| 4,325,939 | 4/1982 | Shah . |
| 4,382,078 | 5/1983 | Berkhoff et al. ......................... 424/42 |
| 4,434,086 | 2/1984 | Hill et al. . |
| 4,434,917 | 3/1984 | Saito et al. . |
| 4,449,987 | 5/1984 | Lindauer . |
| 4,462,880 | 7/1984 | Hill et al. . |
| 4,469,674 | 9/1984 | Shah et al. . |
| 4,488,973 | 12/1984 | Hill et al. . |
| 4,535,152 | 8/1985 | Szejtli et al. . |
| 4,558,821 | 12/1985 | Tada et al. . |
| 4,616,008 | 10/1986 | Hirai et al. . |
| 4,638,058 | 1/1987 | Brandt et al. . |
| 4,678,598 | 7/1987 | Ogino et al. . |
| 4,693,890 | 9/1987 | Wilson et al. . |
| 4,696,676 | 9/1987 | Wilson et al. . |
| 4,727,824 | 3/1988 | Ducharme et al. . |
| 4,735,347 | 4/1988 | Schultz et al. . |
| 4,740,366 | 4/1988 | Winston et al. . |
| 4,746,734 | 5/1988 | Tsuchiyama et al. . |
| 4,761,159 | 8/1988 | Knox . |
| 4,779,803 | 10/1988 | Corsette . |
| 4,818,524 | 4/1989 | Gibbs . |
| 4,819,835 | 4/1989 | Tasaki . |
| 4,840,792 | 6/1989 | Joulain et al. . |
| 4,895,279 | 1/1990 | Schultz . |
| 4,902,434 | 2/1990 | Dickerson . |
| 4,904,639 | 2/1990 | Hallam . |
| 4,933,371 | 6/1990 | Hink et al. . |
| 4,938,416 | 7/1990 | Bertrand et al. ............................ 239/1 |
| 4,946,672 | 8/1990 | Gibbs . |
| 4,992,198 | 2/1991 | Nebashi et al. . |
| 5,008,386 | 4/1991 | Szabo et al. . |
| 5,076,960 | 12/1991 | Hutchings et al. . |
| 5,102,564 | 4/1992 | Gardlik et al. . |
| 5,111,971 | 5/1992 | Winer . |
| 5,135,747 | 8/1992 | Faryniarz et al. . |
| 5,196,200 | 3/1993 | Wilson et al. . |
| 5,211,870 | 5/1993 | Gilbert et al. .......................... 510/153 |
| 5,232,126 | 8/1993 | Winer . |
| 5,234,610 | 8/1993 | Gardlik et al. . |
| 5,234,611 | 8/1993 | Trinh et al. ............................. 510/523 |
| 5,288,423 | 2/1994 | Behan et al. . |
| 5,303,867 | 4/1994 | Peterson .................................. 239/333 |
| 5,420,104 | 5/1995 | Holzner ...................................... 512/2 |
| 5,429,628 | 7/1995 | Trinh et al. ............................. 604/359 |
| 5,554,588 | 9/1996 | Behan et al. . |
| 5,578,563 | 11/1996 | Trinh et al. ............................. 510/513 |
| 5,593,670 | 1/1997 | Trinh et al. ............................. 424/76.1 |
| 5,663,134 | 9/1997 | Trinh et al. ............................. 510/406 |
| 5,668,097 | 9/1997 | Trinh et al. ............................. 510/293 |
| 5,670,475 | 9/1997 | Trinh et al. ............................. 510/470 |
| 5,714,137 | 2/1998 | Trinh et al. ............................. 424/76.4 |
| 5,733,272 | 3/1998 | Brunner et al. ........................ 604/359 |
| 5,783,544 | 7/1998 | Trinh et al. ............................. 510/293 |
| 5,795,566 | 8/1998 | Joulain et al. . |
| 5,939,060 | 8/1999 | Trinh et al. ............................. 424/76.4 |

METHOD OF USING A COMPOSITION FOR REDUCING MALODOR IMPRESSION

This is a continuation of application Ser. No. 08/617,949, filed on Mar. 13, 1996 now U.S. Pat. No. 5,670,475; which is a continuation of application Ser. No. 08/289,731, filed Aug. 12, 1994, now abandoned.

TECHNICAL FIELD

The present invention relates to aqueous, preferably clear, compositions, articles of manufacture and/or method of use, for reducing malodor impression, comprising low levels of perfumes preferably having perfume ingredients with a Clog P of 3 or smaller; optionally, but preferably, water-soluble cyclodextrin, optionally, but preferably, water-soluble metallic salt; and optionally, but preferably, a solubilizing aid. Preferably, the compositions are designed to reduce malodor on inanimate surfaces, especially, clothes, e.g., those that have been stored for a long period of time, that are contaminated with environmental odors such as food odors, tobacco odors, and that are wetted with perspiration. Preferably the composition is used to restore and/or maintain freshness by reducing malodor without the need for washing or dry cleaning.

BACKGROUND OF THE INVENTION

The present invention relates to aqueous, preferably clear, compositions, articles of manufacture, and/or method for use, as a freshening composition. Preferably, the compositions are sprayed onto fabrics, particularly clothes, to restore their freshness by reducing malodor impression, without washing or dry cleaning. Fabrics treated with some preferred compositions of the present invention also release extra fragrance upon rewetting, such as when the wearer perspires. The freshening compositions of the present invention are designed to extend the wear of fabrics between washing or dry cleaning. Fabrics treated with some preferred freshening compositions of the present invention will stay fresher longer, and receive extra freshening effect via perfume release when it is most needed, that is upon fabric rewetting.

Odor masking is the intentional concealment of one odor by the addition of another. The preference to the masking perfume is varied greatly, depending on the application, e.g., underarm odor masking, fabric odor masking, bathroom odor masking, etc. The art teaches the use of perfume as an odor masking device in combination with alcohol in order to solubilize the perfume. It has now been discovered that perfumes with a Clog P of less than 3 do not need alcohol in order to be solubilized.

SUMMARY OF THE INVENTION

The present invention relates to an aqueous composition for reducing malodor impression, comprising:

(A) from about 0.01% to about 1%, by weight of the composition, of perfume wherein the perfume preferably comprises ingredients having a Clog P of 3 or smaller;

(B) optionally, but preferably, from about 0.1% to about 5%, by weight of the composition of, water-soluble cyclodextrin;

(C) optionally, but preferably, from about 0.1% to about 10%, by weight of the composition, of water-soluble metallic salt;

(D) optionally, but preferably, from about 0% to about 3%, by weight of the composition, of solubilizing aid; and (E) aqueous carrier; and wherein said composition is essentially free of any material that would soil or stain fabric and wherein said composition contains less than about 5%, by weight of the composition of low molecular weight monohydric alcohols.

The composition can be incorporated into a spray dispenser to create an article of manufacture that can facilitate treatment of articles and/or surfaces with the composition to reduce malodor at a level that is effective, yet is not discernible when dried on the surface.

DETAILED DESCRIPTION OF THE INVENTION

The present invention relates to an aqueous composition for reducing malodor impression, comprising:

(A) from about 0.01% to about 1%, by weight of the composition, of perfume wherein the perfume preferably comprises ingredients having a Clog P of 3 or smaller;

(B) optionally, but preferably, from about 0.1% to about 5%, by weight of the composition of, water-soluble cyclodextrin;

(C) optionally, but preferably, from about 0.1% to about 10%, by weight of the composition, of water-soluble metallic salt;

(D) optionally, but preferably, from about 0% to about 3%, by weight of the composition, of solubilizing aid; and (E) aqueous carrier; and wherein said composition is essentially free of any material that would soil or stain fabric and wherein said composition contains less than about 5%, by weight of the composition of low molecular weight monohydric alcohols.

I. Composition (A) Perfume

The perfume selected for use in the fabric freshening composition of the present invention contains ingredients with odor characteristics which are preferred in order to provide a fresh impression on the surface to which the composition is directed, preferably those which provide a fresh impression for fabrics.

Preferably, at least about 25%, more preferably at least about 50%, most preferably at least about 75%, by weight of the perfume is composed of fragrance material selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and essentially free from nitromusks and halogenated fragrance materials.

More preferably, at least about 25%, more preferably at least about 50%, most preferably at least about 75%, by weight of the perfume is composed of fragrance material selected from the group consisting of:

| Common Name | Chemical Type | Chemical Name | Approx. M.W. |
| --- | --- | --- | --- |
| adoxal | aliphatic aldehyde | 2,6,10-trimethyl-9-undecen-1-al | 210 |
| allyl amyl glycolate | ester | allyl amyl glycolate | 182 |
| allyl cyclohexane propionate | ester | allyl-3-cyclohexyl propionate | 196 |
| amyl acetate | ester | 3-methyl-1-butanol acetate | 130 |
| amyl salicylate | ester | amyl salicylate | 208 |
| anisic aldehyde | aromatic aldehyde | 4-methoxy benzaldehyde | 136 |
| aurantiol | schiff base | condensation product of methyl anthranilate and hydroxycitronellal | 305 |
| bacdanol | aliphatic alcohol | 2-ethyl-4-(2,2,3-trimethyl-3-cyclopenten-1-yl)-2-buten-1-ol | 208 |
| benzaldehyde | aromatic aldehyde | benzaldehyde | 106 |
| benzophenone | aromatic ketone | benzophenone | 182 |
| benzyl acetate | ester | benzyl acetate | 150 |
| benzyl salicylate | ester | benzyl salicylate | 228 |
| beta damascone | aliphatic ketone | 1-(2,6,6-trimethyl-1-cyclo-hexen-1-yl)-2-buten-1-one | 192 |
| beta gamma hexanol | alcohol | 3-hexen-1-ol | 100 |
| buccoxime | aliphatic ketone | 1,5-dimethyl-oxime bicyclo[3,2,1] octan-8-one | 167 |
| cedrol | alcohol | octahydro-3,6,8,8-tetramethyl-IH-3A,7-methanoazulen-6-ol | 222 |
| cetalox | ether | dodecahydro-3A,6,6,9A-tetramethylnaphtho[2,1B]-furan | 236 |
| cis-3-hexenyl acetate | ester | cis-3-hexenyl acetate | 142 |
| cis-3-hexenyl salicylate | ester | beta, gamma-hexenyl salicylate | 220 |
| citronellol | alcohol | 3,7-dimethyl-6-octenol | 156 |
| citronellyl nitrile | nitrile | geranyl nitrile | 151 |
| clove stem oil | natural | | |
| coumarin | lactone | coumarin | 146 |
| cyclohexyl salicylate | ester | cyclohexyl salicylate | 220 |
| cymal | aromatic aldehyde | 2-methyl-3-(para iso propyl phenyl)propionaldehyde | 190 |
| decyl aldehyde | aliphatic aldehyde | decyl aldehyde | 156 |
| delta damascone | aliphatic ketone | 1-(2,6,6-trimethyl-3-cyclo-hexen-1-yl)-2-buten-1-one | 192 |
| dihydromyrcenol | alcohol | 3-methylene-7-methyl octan-7-ol | 156 |
| dimethyl benzyl carbinyl acetate | ester | dimethyl benzyl carbinyl acetate | 192 |
| ethyl vanillin | aromatic aldehyde | ethyl vanillin | 166 |
| ethyl-2-methyl butyrate | ester | ethyl-2-methyl butyrate | 130 |
| ethylene brassylate | macrocyclic lactone | ethylene tridecan-1,13-dioate | 270 |
| eucalyptol | aliphatic epoxide | 1,8-epoxy-para-menthane | 154 |
| eugenol | alcohol | 4-allyl-2-methoxy phenol | 164 |
| exaltolide | macrocyclic lactone | cyclopentadecanolide | 240 |
| flor acetate | ester | dihydro-nor-cyclopentadienyl acetate | 190 |
| florhydral | aromatic aldehyde | 3-(3-isopropylphenyl)butanal | 190 |
| frutene | ester | dihydro-nor-cyclopentadienyl propionate | 206 |
| galaxolide | ether | 1,3,4,6,7,8-hexahydro-4,6,6,7,8,8-hexamethylcyclopenta-gamma-2-benzopyrane | 258 |
| gamma decalactone | lactone | 4-N-hepty-4-hydroxybutanoic acid lactone | 170 |
| gamma dodecalactone | lactone | 4-N-octyl-4-hydroxy-butanoic acid lactone | 198 |
| geraniol | alcohol | 3,7-dimethyl-2,6-octadien-1-ol | 154 |
| geranyl acetate | ester | 3,7-dimethyl-2,6-octadien-1-yl acetate | 196 |
| geranyl nitrile | ester | 3,7-diemthyl-2,6-octadienenitrile | 149 |
| helional | aromatic aldehyde | alpha-methyl-3,4, (methylenedioxy) hydrocinnamaldehyde | 192 |
| heliotropin | aromatic aldehyde | heliotropin | 150 |
| hexyl acetate | ester | hexyl acteate | 144 |
| hexyl cinnamic aldehyde | aromatic aldehyde | alpha-n-hexyl cinnamic aldehyde | 216 |
| hexyl salicylate | ester | hexyl salicylate | 222 |
| hydroxyambran | aliphatic alcohol | 2-cyclododecyl-propanol | 226 |
| hydroxycitronellal | aliphatic aldehdye | hydroxycitronellal | 172 |
| ionone alpha | aliphatic ketone | 4-(2,6,6-trimethyl-1-cyclohexenyl-1-yl)-3-buten-2-one | 192 |
| ionone beta | aliphatic ketone | 4-(2,6,6-trimethyl-1-cyclohexen- | 192 |

-continued

| Common Name | Chemical Type | Chemical Name | Approx. M.W. |
|---|---|---|---|
| ionone gamma methyl | aliphatic ketone | 4-(2,6,6-trimethyl-2-cyclohexyl-1-yl)-3-butene-2-one 1-yl)-3-methyl-3-buten-2-one | 206 |
| iso E super | aliphatic ketone | 7-acetyl-1,2,3,4,5,6,7,8-octahydro-1,1,6,7,tetramethyl naphthalene | 234 |
| iso eugenol | ether | 2-methoxy-4-(1-propenyl) phenol | 164 |
| iso jasmone | aliphatic ketone | 2-methyl-3-(2-pentenyl)-2-cyclopenten-1-one | 166 |
| koavone | aliphatic aldehyde | acetyl di-isoamylene | 182 |
| lauric aldehyde | aliphatic aldehyde | lauric aldehyde | 184 |
| lavandin | natural | | |
| lavender | natural | | |
| lemon CP | natural | major component d-limonene | |
| d-limonene/orange terpenes | alkene | 1-methyl-4-iso-propenyl-1-cyclohexene | 136 |
| linalool | alcohol | 3-hydroxy-3,7-dimethyl-1,6-octadiene | 154 |
| linalyl acetate | ester | 3-hydroxy-3,7-dimethyl-1,6-octadiene acetate | 196 |
| lrg 201 | ester | 2,4-dihydroxy-3,6-dimethyl benzoic acid methyl ester | 196 |
| lyral | aliphatic aldehyde | 4-(4-hydroxy-4-methyl-pentyl) 3-cylcohexene-1-carboxaldehyde | 210 |
| majantol | aliphatic alcohol | 2,2-dimethyl-3-(3-methylphenyl)-propanol | 178 |
| mayol | alcohol | 4-(1-methylethyl) cyclohexane methanol | 156 |
| methyl anthranilate | aromatic amine | methyl-2-aminobenzoate | 151 |
| methyl beta naphthyl ketone | aromatic ketone | methyl beta naphthyl ketone | 170 |
| methyl cedrylone | aliphatic ketone | methyl cedrenyl ketone | 246 |
| methyl chavicol | ester | 1-methyloxy-4,2-propen-1-yl benzene | 148 |
| methyl dihydro jasmonate | aliphatic ketone | methyl dihydro jasmonate | 226 |
| methyl nonyl acetaldehyde | aliphatic aldehyde | methyl nonyl acetaldehyde | 184 |
| musk indanone | aromatic ketone | 4-acetyl-6-tert butyl-1,1-dimethyl indane | 244 |
| nerol | alcohol | 2-cis-3,7-dimethyl-2,6-octadien-1-ol | 154 |
| nonalactone | lactone | 4-hydroxynonanoic acid, lactone | 156 |
| norlimbanol | aliphatic alcohol | 1-(2,2,6-trimethyl-cyclohexyl)-3-hexanol | 226 |
| orange CP | natural | major component d-limonene | |
| P. T. bucinal | aromatic aldehyde | 2-methyl-3(para tert butylphenyl) propionaldehyde | 204 |
| para hydroxy phenyl butanone | aromatic ketone | para hydroxy phenyl butanone | 164 |
| patchouli | natural | | |
| phenyl acetaldehyde | aromatic aldehyde | 1-oxo-2-phenylethane | 120 |
| phenyl acetaldehyde dimethyl acetal | aromatic aldehyde | phenyl acetaldehyde dimethyl acetal | 166 |
| phenyl ethyl acetate | ester | phenyl ethyl acetate | 164 |
| phenyl ethyl alcohol | alcohol | phenyl ethyl alcohol | 122 |
| phenyl ethyl phenyl acetate | ester | 2-phenylethyl phenyl acetate | 240 |
| phenyl hexanol/phenoxanol | alcohol | 3-methyl-5-phenylpentanol | 178 |
| polysantol | aliphatic alcohol | 3,3-dimethyl-5-(2,2,3-trimethyl-3-cyclopenten-1-yl)-4-penten-2-ol | 221 |
| prenyl acetate | ester | 2-methylbuten-2-ol-4-acetate | 128 |
| rosaphen | aromatic alcohol | 2-methyl-5-phenyl pentanol | 178 |
| sandalwood | natural | | |
| alpha-terpinene | aliphatic alkane | 1-methyl-4-iso-propylcyclohexadiene-1,3 | 136 |
| terpineol (alpha terpineol and beta terpineol) | alcohol | para-menth-1-en-8-ol, para-menth-1-en-1-ol | 154 |
| terpinyl acetate | ester | para-menth-1-en-8-yl acetate | 196 |
| tetra hydro linalool | aliphtic alcohol | 3,7-dimethyl-3-octanol | 158 |
| tetrahydromyrcenol | aliphatic alcohol | 2,6-dimethyl-2-octanol | 158 |
| tonalid/musk plus | aromatic ketone | 7-acetyl-1,1,3,4,4,6-hexamethyl tetralin | 258 |
| undecalactone | lactone | 4-N-heptyl-4-hydroxybutanoic acid lactone | 184 |
| undecavertol | alcohol | 4-methyl-3-decen-5-ol | 170 |
| undecyl aldehyde | aliphatic aldehyde | undecanal | 170 |
| undecylenic aldehyde | aliphatic aldehyde | undecylenic aldehyde | 168 |

-continued

| Common Name | Chemical Type | Chemical Name | Approx. M.W. |
| --- | --- | --- | --- |
| vanillin | aromatic aldehyde | 4-hydroxy-3-methoxybenzaldehyde | 152 |
| verdox | ester | 2-tert-butyl cyclohexyl acetate | 198 |
| vertenex | ester | 4-tert-butyl cyclohexyl acetate | 198 | and mixtures thereof.

When high initial perfume odor impact on fabrics is desired, it is also preferable to select a perfume containing perfume ingredients which are not too hydrophobic. The less hydrophobic perfume ingredients are more soluble in water, and are more available in the freshening composition. The degree of hydrophobicity of a perfume ingredient can be correlated with its octanol/water partitioning coefficient P. The octanol/water partitioning coefficient of a perfume ingredient is the ratio between its equilibrium concentration in octanol and in water. A perfume ingredient with a greater partitioning coefficient P is more hydrophobic. Conversely, a perfume ingredient with a smaller partitioning coefficient P is more hydrophilic. The preferred perfume ingredients of this invention have an octanol/water partitioning coefficient P of about 1,000 or smaller. Since the partitioning coefficients of the perfume ingredients normally have high values, they are more conveniently given in the form of their logarithm to the base 10, logP. Thus the perfume ingredients of this invention have logP of about 3 or smaller.

The logP of many perfume ingredients has been reported; for example, the Pomona 92 database, available from Daylight Chemical Information Systems, Inc. (Daylog CIS), Irvine, Calif., contains many, along with citations to the original literature. However, the logP values are most conveniently calculated by the "CLOG P" program, also available from Daylight CIS. This program also lists experimental logP values when they are available in the Pomona 92 database. The "calculated logP" (Clog P) is determined by the fragment approach of Hansch and Leo (cf, A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The Clog P values, which are the most reliable and widely used estimates for this physicochemical property, are used instead of the experimental logP values in the selection of perfume ingredients which are useful in the present invention.

Non-limiting examples of perfume ingredients which have Clog P values of about 3 or smaller are benzaldehyde, benzyl acetate, cis-3-hexenyl acetate, coumarin, dihydromyrcenol, dimethyl benzyl carbinyl acetate, ethyl vanillin, eucalyptol, eugenol, iso eugenol, flor acetate, geraniol, hydroxycitronellal, linalool, methyl anthranilate, methyl beta naphthyl ketone, methyl dihydro jasmonate, nerol, nonalactone, phenyl ethyl acetate, phenyl ethyl alcohol, alpha terpineol, beta terpineol, vanillin, and mixtures thereof.

When hydrophilic perfume is desired, at least about 25% by weight of the perfume, more preferably about 50%, most preferably about 75%, is composed of perfume ingredients having a Clog P of about 3 or smaller.

Preferably the freshening composition contains an effective amount of perfume to provide the freshening fragrance to fabrics when first sprayed, some lingering fragrance in-wear, and some extra fragrance to be released upon fabric rewetting. Effective level of perfume is from about 0.01% to about 1%, more preferably from about 0.01% to about 0.5%, most preferably from about 0.015% to about 0.3%, by weight of the composition. When cyclodextrin is added to the composition of the present invention, the perfume to cyclodextrin weight ratio is typically from about 3:100 to about 100:100, preferably from about 4:100 to about 50:100, more preferably from about 5:100 to about 40:100, even more preferably from about 5 100 to about 25:100, most preferably from about 1:8 to about 1:4.

(B) Cyclodextrin

Optionally, but preferably, solubilized, water-soluble, uncomplexed cyclodextrin can be added to the composition of the present invention. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Non-derivatised (normal) beta-cyclodextrin can be used although it is not preferred due to its low solubility. When non-derivatised beta-cyclodextrin is used, the aqueous solution becomes cloudy and is not clear, as preferred by the present invention. Not to be limited by theory, it is believed that some beta-cyclodextrin and/or beta-cyclodextrin/perfume complexes solidify and/or precipitate out producing an undesirable cloudy aqueous solution.

Preferably, the odor absorbing solution of the present invention is clear. The term "clear" as defined herein means transparent or translucent, preferably transparent as in "water clear," when observed through a layer having a thickness of less than about 10 cm.

Preferably, the cyclodextrins used in the present invention are highly water-soluble such as, alpha-cyclodextrin and derivatives thereof, gamma-cyclodextrin and derivatives thereof, derivatised beta-cyclodextrins, and/or mixtures thereof The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —CH$_2$—CH(OH)—CH$_3$ or a —CH$_2$CH$_2$—OH group; branched cyclodextrins such as maltose-bonded cyclodextrins; cationic cyclodextrins such as those containing 2-hydroxy-3 (dimethylamino)propyl ether, wherein R is CH$_2$—CH(OH)—CH$_2$—N(CH$_3$)$_2$ which is cationic at low pH; quaternary ammonium, e.g., 2-hydroxy-3-(trimethylammonio) propyl ether chloride groups, wherein R is CH$_2$—CH(OH)—CH$_2$—N$^+$(CH$_3$)$_3$Cl$^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, herein incorporated by reference; and mixtures thereof Other cyclodextrin derivatives are disclosed in U.S. Pat. No: 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available methylated beta-cyclodextrin is a randomly methylated beta-cyclodextrin having a degree of substitution of about 12.6. The preferred cyclodextrins are available, e.g., from American Maize-Products Company and Wacker Chemicals (U.S.A.), Inc.

It is also preferable to use a mixture of cyclodextrins. Such mixtures can complex with a wider range of perfume molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, and mixtures thereof.

Cyclodextrin molecules are known for their ability to form complexes with perfume ingredients and have typically been taught as a perfume carrier. The prior art teaches the use of drier-added fabric softener sheets containing high levels of cyclodextrin/perfume complexes wherein the fabrics treated with this solid cyclodextrin complex release perfume when the fabrics are rewetted. The art also teaches that cyclodextrin/perfume complexes used in aqueous rinse-added fabric softener compositions must be protected, e.g., with a hydrophobic wax coating so the cyclodextrin/perfume complexes will not decompose due to the presence of water. See U.S. Pat. No. 5,102,564 Gardlik et al., issued Apr. 7, 1992; U.S. Pat. No. 5,234,610, Gardlik et al., issued Aug. 10, 1993; U.S. Pat. No. 5,234,611 Trinh, et al., issued Aug. 10, 1993, all of said patents incorporated herein by reference. It is therefore highly surprising and unexpected to find that fabrics treated with the aqueous compositions of the present invention, which contain low levels of unprotected cyclodextrin, also exhibit perfume release upon rewetting. This phenomenon provides a benefit in that fabrics treated with the composition of the present invention will thus remain fresh longer, via a perfume release, when said fabrics are rewetted, such as when the wearer perspires.

For reducing malodor impression on fabrics, the composition is preferably used as a spray. It is preferable that the composition of the present invention contain low levels of cyclodextrin so that a visible stain does not appear on the fabric at normal usage levels. Preferably, the solution is not discernible when dry. Typical levels of cyclodextrin are from about 0.1% to about 5%, preferably from about 0.2% to about 4%, more preferably from about 0.3% to about 3%, most preferably from about 0.4% to about 2%, by weight of the composition. Compositions with higher concentrations can leave unacceptable visible stains on fabrics as the solution evaporates off of the fabric. This is especially a problem on thin, colored, synthetic fabrics. In order to avoid or minimize the occurrence of fabric staining, it is preferable that the fabric be treated at a level of less than about 5 mg of cyclodextrin per mg of fabric, more preferably less than about 2 mg of cyclodextrin per mg of fabric.

Concentrated compositions can also be used in order to provide a less expensive product. When a concentration is used, i.e., when the level of cyclodextrin used is from about 3% to about 5%, it is preferable to dilute the composition before treating fabrics in order to avoid staining. Preferably the cyclodextrin is diluted with about 50% to about 2000%, more preferably with about 60% to about 1000%, most preferably with about 75% to about 500%, by weight of the composition, of water.

(C) Metallic Salt

Optionally, but preferably, metallic salt, preferably water-soluble zinc salts, can be added to the composition of the present invention. A water-soluble metallic salt can be used as an odor control agent. A water-soluble metallic salt can be present in the freshening composition of the present invention to absorb amine and sulfur-containing compounds. Furthermore, they usually do not contribute an odor of their own. Preferably the water-soluble metallic salts are selected from the group consisting of copper salts, zinc salts, and mixtures thereof The preferred zinc salts have been used most often for their ability to ameliorate malodor, e.g., in mouth wash products, as disclosed in U.S. Pat. No. 4,325,939, issued Apr. 20, 1982 and U.S. Pat. No. 4,469,674, issued Sep. 4, 1983, to N. B. Shah, et al., incorporated herein by reference. U.S. Pat. No. 3,172,817, issued to Leupold, et al., discloses deodorizing compositions containing slightly water-soluble salts of an acyl-acetone with a polyvalent metal, including copper and zinc salts. Said patents are incorporated herein by reference.

Examples of preferred water-soluble zinc salts are zinc chloride, zinc gluconate, zinc lactate, zinc maleate, zinc salicylate, zinc sulfate, etc. Highly-ionized and soluble zinc salts such as zinc chloride, provide the best source of zinc ions. Examples of preferred copper salts are copper chloride and copper gluconate. Preferred metallic salts are zinc chloride and copper chloride.

Metallic salts are added to the composition of the present invention typically at a level of from about 0.1% to about 10%, preferably from about 0.2% to about 7%, more preferably from about 0.3% to about 5%, by weight of the composition. When zinc salts are used as the metallic salt, and a clear solution is desired, it is preferable that the pH of the solution is adjusted to less than about 7, more preferably less than about 6, most preferably, less than about 5, in order to keep the solution clear.

(D) Solubilizing Aid

The freshening composition of the present invention can optionally, but preferably, contain a solubilizing aid to solubilize any excess hydrophobic organic materials, especially the perfume, and also optional ingredients which can be added to the composition, e.g., insect repelling agent, antioxidant, etc., that are not readily soluble in the composition, to form a clear solution. A suitable solubilizing aid is surfactant, preferably no-foaming or low-foaming surfactant. Suitable surfactants are nonionic surfactants, cationic surfactants, amphoteric surfactants, zwitterionic surfactants, and mixtures thereof, preferably nonionic surfactants and cationic surfactants, and mixtures thereof Anionic surfactants are not preferred, because they can form water-insoluble salts with the metal ions of the preferred metallic salts of this composition. Suitable surfactants can be emulsifiers and/or detersive surfactants. Mixtures of emulsifiers and detersive surfactants are also preferred. When a surfactant containing one, or more, alkyl group is used, it is preferred that it contain relatively short alkyl chains of from about 5 to about 14 carbon atoms. Preferred nonionic surfactants are polyethylene glycol-polypropylene glycol block copolymers, such as Pluronic® and Pluronic R® surfactants from BASF; Tetronic(® and Tetronic R® surfactants from BASF, ethoxylated branched aliphatic diols, such as Surfynol® surfactants from Air Products; ethoxylated alkyl phenols, such as Igepal® surfactants from Rhône-Poulenc; ethoxylated aliphatic alcohols and carboxylic acids; polyethylene glycol diesters of fatty acids; fatty acid esters of ethoxylated sorbitans; and mixtures thereof Preferred cationic surfactants are di($C_8$–$C_{12}$ alkyl)di(C1–C2 alkyl)ammonium halides, alkylbenzyldimethylammonium halides, amine oxides, and mixtures thereof Preferred amphoteric surfactants are the betaines. It is preferred that the surfactant have good wetting properties. Also preferred are surfactants that have the hydrophilic groups between hydrophobic chains, such as, Pluronic R surfactants, Surfynol surfactants, polyethylene glycol diesters of fatty acids, fatty acid esters of ethoxylated sorbitans, di($C_8$–$C_{12}$ alkyl) di(C1–C2 alkyl)ammonium halides, and mixtures thereof; surfactants that have hydrophilic groups situated at the extremities of the hydrophobic chain, such as Pluronic surfactants; and mixtures thereof Mixtures of these surfactants and other types of surfactants are also preferred to form no-foaming or low-foaming solubilizing agents. Polyalkylene glycol can be used as defoaming agent in combination with the solubilizing agents.

When the solubilizing agent is present, it is typically present at a level of from about 0.05% to about 3%, by weight of the composition, more preferably from about 0.05% to about 1%, by weight of the composition, most preferably from about 0.1% to about 0.3%, by weight of the composition.

(E) Aqueous Carrier

Aqueous solutions are preferred in the present invention for the reduction of malodor impression. The preferred aqueous carrier of the present invention is water. The water which is used can be distilled, deionized, or tap water, Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, it is preferably that the level of monohydric alcohol be less than about 5%, preferably less than about 3%, more preferably less than about 1%, by weight of the composition.

It has recently been discovered that water has an unexpected odor controlling effect of its own. It has been discovered that the intensity of the odor generated by some polar, low molecular weight organic amines, acids, and mercaptans is reduced when the odor-contaminated fabrics are treated with an aqueous solution. Not to be bound by theory, it is believed that water solubilizes and depresses the vapor pressure of these polar, low molecular weight organic molecules, thus reducing their odor intensity.

(F) Other Optional Ingredients

Adjuvants can be optionally added to the freshening composition herein for their known purposes. Such adjuvants include, but are not limited to, preservatives, defoaming agents, antifoaming agents, bacteriocides, fungicides, antistatic agents, insect and moth repelling agents, colorants, especially bluing agents, antioxidants, and mixtures thereof.

(1) Preservative

Optionally, solubilized, water-soluble preservatives can be added to the present invention. Preservatives are especially preferred when cyclodextrin is added to the composition of the present invention because cyclodextrin molecules are made up of varying numbers of glucose units which can make them a prime breeding ground for certain microorganisms, especially when in aqueous compositions. This drawback can lead to the problem of storage stability of cyclodextrin solutions for any significant length of time. Contamination by certain microorganisms with subsequent microbial growth resulting in an unsightly and/or malodorous solution. Because microbial growth in cyclodextrin solutions is highly objectionable when it occurs, it is preferable to include a solubilized water-soluble, antimicrobial preservative, which is effective for inhibiting and/or regulating microbial growth in order to increase storage stability of the preferably clear, aqueous odor-absorbing solution containing water-soluble cyclodextrin.

Typical microorganisms that can be found in cyclodextrin supplies and whose growth can be found in the presence of cyclodextrin in aqueous cyclodextrin solutions include bacteria, e.g., *Bacillus thuringiensis* (cereus group) and *Bacillus sphaericus*, and fungi, e.g., *Aspergillus ustus*. *Bacillus sphaericus* is one of the most numerous members of Bacillus species in soils. *Aspergillus ustus* is common in grains and flours which are raw materials to produce cyclodextrins. Microorganisms such as *Escherichia coli* and *Pseudomonas aeruginosa* are found in some water sources, and can be introduced during the preparation of cyclodextrin aqueous solutions.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used.

Antimicrobial preservatives useful in the present invention can be biocidal compounds, i.e., substances that kill microorganisms, or biostatic compounds, i.e., substances that inhibit and/or regulate the growth of microorganisms.

Preferred antimicrobial preservatives are those that are water-soluble and are effective at low levels because the organic preservatives can form inclusion complexes with the cyclodextrin molecules and compete with the perfume molecules for the cyclodextrin cavities, thus rendering the complexed preservatives much less effective. Water-soluble preservatives useful in the present invention are those that have a solubility in water of at least about 0.3 g per 100 ml of water, i.e., about 0.3% at room temperature, preferably greater than about 0.5% at room temperature. These types of preservatives have a lower affinity to the cyclodextrin cavity, at least in the aqueous phase, and are therefore more available to provide antimicrobial activity. Preservatives with a water-solubility of less than about 0.3% and a molecular structure that readily fits into the cyclodextrin cavity, have a greater tendency to form inclusion complexes with the cyclodextrin molecules, thus rendering the preservative less effective to control microbes in the cyclodextrin solution. Therefore, many well known preservatives such as short chain alkyl esters of p-hydroxybenzoic acid, commonly known as parabens; N-(4-chlorophenyl)-N'-(3,4-dichlorophenyl)urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with cyclodextrin.

The water-soluble antimicrobial preservative is included in the present invention it is included at an effective amount. The term "effective amount" as herein defined means a level sufficient to prevent spoilage or prevent growth of inadvertently added microorganisms for a specific period of time, but not sufficient enough to contribute to the odor absorbing performance of the composition. In other words, the preservative is not being used to kill microorganisms on the surface onto which the composition is deposited in order to eliminate odors produced by microorganisms. Instead, it is preferably being used to prevent spoilage of the cyclodextrin solution in order to increase the shelf-life of the composition. Preferred levels of preservative are from about 0.0001% to about 0.5%, more preferably from about 0.0002% to about 0.2%, most preferably from about 0.0003% to about 0.1%, by weight of the composition.

The preservative can be any organic preservative material which will not cause damage to fabric appearance, e.g., discoloration, coloration, bleaching. Preferred water-soluble preservatives include organic sulfur compounds, halogenated compounds, cyclic organic nitrogen compounds, low molecular weight aldehydes, quaternary compounds, dehydroacetic acid, phenyl and phenoxy compounds, and mixtures thereof Non-limiting examples of the preferred water-soluble preservatives for use in the present invention include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the trade name Bronidox L® from Henkel; 2-bromo-2-nitropropane-1,3-diol, available under the trade name Bronopol® from Inolex; 1,1'-hexamethylene bis(5-(p-chlorophenyl) biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N, N'-bis(hydroxymethyl)urea, commonly known as diazolidinyl urea, available under the trade name Germall II® from Sutton Laboratories, Inc.; N,N"-methylenebis(N'-[1-(hydroxymethyl)-2,5-dioxo-4-imidazolidinyl]urea), commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide; available under the trade name Cosmocil CQ® from ICI Americas, Inc., or under the trade name Mikrokill® from Brooks, Inc; dehydroacetic acid; and mixtures thereof Bacteriostatic effects can sometimes be obtained for aqueous compositions by adjusting the composition pH to an acid pH, e.g., less than about pH 4, preferably less than about pH 3. Low pH for microbial control is not a preferred approach in the present invention because the low pH can cause chemical degradation of the cyclodextrins. Therefore, aqueous compositions of the present invention should have a pH greater than about 3.0, preferably greater than about 4.0, more preferably greater than about 4.5.

As stated above, it is preferable to use the preservative at an effective amount, as defined hereinabove. Optionally however, the preservative can be used at a level which provides an antimicrobial effect on the treated fabrics.

(2) Antistatic Agents

The composition of the present invention can optionally contain an effective amount of antistatic agent to provide the treated clothes with in-wear static. Preferred antistatic agents are those that are water soluble in at least effective amount, such that the composition remains a clear solution. Examples of these antistatic agents are monoalkyl cationic quaternary ammonium compounds, e.g., mono($C_{10}$–$C_{14}$ alkyl)trimethyl ammonium halide, such as monolauryl trimethyl ammonium chloride, hydroxycetyl hydroxyethyl dimethyl ammonium chloride, available under the trade name Dehyquart E® from Henkel, and ethyl bis(polyethoxy ethanol) alkylammonium ethylsulfate, available under the trade name Variquat 66® from Witco Corp., polyethylene glycols, polymeric quaternary ammonium salts, such as polymers conforming to the general formula:

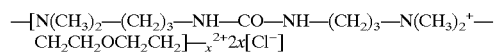

available under the trade name Mirapol A-15® from Rhône-Poulenc, and

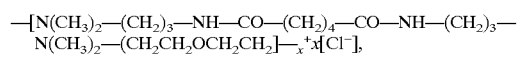

available under the trade name Mirapol AD-1® from Rhône-Poulenc, quaternized polyethyleneimines, vinylpyrrolidone/methacrylamidopropyltrimethylammonium chloride copolymer, available under the trade name Gafquat HS-100® from GAF; triethonium hydrolyzed collagen ethosulfate, available under the trade name Quat-Pro E® from Maybrook; and mixtures thereof.

It is preferred that a no foaming, or low foaming, agent is used, to avoid foam formation during fabric treatment. It is also preferred that polyethoxylated agents such as polyethylene glycol or Variquat 66® are not used when alpha-cyclodextrin is used. The polyethoxylate groups have a strong affinity to, and readily complex with, alpha-cyclodextrin which in turn deplete the uncomplexed cyclodextrin available for the perfume.

When an antistatic agent is used it is typically present at a level of from about 0.05% to about 10%, preferably from about 0.1% to about 5%, more preferably from about 0.3% to about 3%, by weight of the composition.

(3) Insect and/or Moth Repelling Agent

The composition of the present invention can optionally contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citranellal, citral, linalool, cedar extract, geranium oil, sandalwood oil, 2-(diethylphenoxy)ethanol, 1-dodecene, etc. Other examples of insect and/or moth repellents useful in the composition of the present invention are disclosed in U.S. Pat. Nos. 4,449,987, 4,693,890, 4,696, 676, 4,933,371, 5,030,660, 5,196,200, and in "Semio Activity of Flavor and Fragrance Molecules on Various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35–48, all of said patents and publications incorporated herein by reference. When an insect and/or moth repellent is used it is typically present at a level of from about 0.005% to about 3%, by weight of the composition.

(4) Colorant

Colorants and dyes, especially bluing agents, can be optionally added to the odor absorbing compositions for visual appeal and performance impression. When colorants are used, they are used at extremely low levels to avoid fabric staining. Preferred colorants for use in the present compositions are highly water-soluble dyes, e.g., Liquitint® dyes available from Milliken Chemical Co. Non-limiting examples of suitable dyes are, Liquitint Blue HP®, Liquitint Blue 65®, Liquitint Patent Blue®, Liquitint Royal Blue®, Liquitint Experimental Yellow 8949-43®, Liquitint Green HMC®, Liquitint Yellow II®, and mixtures thereof, preferably Liquitint Blue HP®, Liquitint Blue 65®, Liquitint Patent Blue®, Liquitint Royal Blue®, Liquitint Experimental Yellow 8949-43®, and mixtures thereof II. Article of Manufacture The composition of the present invention can also be used in an article of manufacture comprising said composition plus a spray dispenser.

Spray Dispenser

The article of manufacture herein comprises a spray dispenser. The composition for reducing malodor impression is placed into a spray dispenser in order to be distributed onto the fabric. Said spray dispenser is any of the manually activated means for producing a spray of liquid droplets as is known in the art, e.g. trigger-type, pump-type, non-aerosol self-pressurized, and aerosol-type spray means. The spray dispenser herein does not include those that will substantially foam the clear, aqueous composition. It is preferred that at least about 80%, more preferably, at least about 90% of the droplets have a particle size of larger than about 30 $\mu$m The spray dispenser can be an aerosol dispenser. Said aerosol dispenser comprises a container which can be constructed of any of the conventional materials employed in fabricating aerosol containers. The dispenser must be capable of withstanding internal pressure in the range of from about 20 to about 110 p.s.i.g., more preferably from about 20 to about 70 p.s.i.g. The one important requirement concerning the dispenser is that it be provided with a valve member which will permit the clear, aqueous odor absorbing composition contained in the dispenser to be dispensed in the form of a spray of very fine, or finely divided, particles or droplets. The aerosol dispenser utilizes a pressurized sealed container from which the clear, aqueous odor-absorbing composition is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, are not preferred. Halogenated hydrocarbon propellants such as chlorofluoro hydrocarbons have been alleged to contribute to environmental problems. Hydrocarbon propellants can form complexes with the cyclodextrin molecules thereby reducing the availability of uncomplexed cyclodextrin molecules for odor absorption. Preferred propellants are compressed air, nitrogen, inert gases, carbon dioxide, etc. A more complete description of commercially available aerosol-spray dispensers appears in U.S. Pat. No. 3,436,772, Stebbins, issued Apr. 8, 1969; and U.S. Pat. No. 3,600,325, Kaufman et al., issued Aug. 17, 1971; both of said references are incorporated herein by reference.

Preferably the spray dispenser can be a self-pressurized non-aerosol container having a convoluted liner and an elastomeric sleeve. Said self-pressurized dispenser comprises a liner/sleeve assembly containing a thin, flexible radially expandable convoluted plastic liner of from about 0.010 to about 0.020 inch thick, inside an essentially cylindrical elastomeric sleeve. The liner/sleeve is capable of holding a substantial quantity of odor-absorbing fluid product and of causing said product to be dispensed. A more complete description of self-pressurized spray dispensers can be found in U.S. Pat. No. 5,111,971, Winer, issued May 12, 1992, and U.S. Pat. No. 5,232,126, Winer, issued Aug. 3, 1993; both of said references are herein incorporated by reference. Another type of aerosol spray dispenser is one wherein a barrier separates the odor absorbing composition from the propellant (preferably compressed air or nitrogen), as disclosed in U.S. Pat. No. 4,260,110, issued Apr. 7, 1981, and incorporated herein by reference. Such a dispenser is available from EP Spray Systems, East Hanover, N.J.

More preferably, the spray dispenser is a non-aerosol, manually activated, pump-spray dispenser. Said pump-spray dispenser comprises a container and a pump mechanism which securely screws or snaps onto the container. The container comprises a vessel for containing the aqueous odor-absorbing composition to be dispensed.

The pump mechanism comprises a pump chamber of substantially fixed volume, having an opening at the inner end thereof Within the pump chamber is located a pump stem having a piston on the end thereof disposed for reciprocal motion in the pump chamber. The pump stem has a passageway there through with a dispensing outlet at the outer end of the passageway and an axial inlet port located inwardly thereof The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. A preferred container is made of clear, e.g., polyethylene terephthalate. Other materials can include stainless steel. A more complete disclosure of commercially available dispensing devices appears in: U.S. Pat. No. 4,895,279, Schultz, issued Jan. 23, 1990; U.S. Pat. No. 4,735,347, Schultz at al. issued Apr. 5, 1988; and U.S. Pat. No. 4,274,560, Carter, issued Jun. 23, 1981; all of said references are herein incorporated by reference.

Most preferably, the spray dispenser is a manually activated trigger-spray dispenser. Said trigger-spray dispenser comprises a container and a trigger both of which can be constructed of any of the conventional material employed in fabricating trigger-spray dispensers, including, but not limited to: polyethylene, polypropylene, polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear, e.g. polyethylene terephthalate. The trigger-spray dispenser does not incorporate a propellant gas into the odor-absorbing composition, and preferably it does not include those that will foam the odor-absorbing composition. The trigger-spray dispenser herein is typically one which acts upon a discrete amount of the odor-absorbing composition itself, typically by means of a piston or a collapsing bellows that displaces the composition through a nozzle to create a spray of thin liquid. Said trigger-spray dispenser typically comprises a pump chamber having either a piston or bellows which is movable through a limited stroke response to the trigger for varying the volume of said pump chamber. This pump chamber or bellows chamber collects and holds the product for dispensing. The trigger spray dispenser typically has an outlet check valve for blocking communication and flow of fluid through the nozzle and is responsive to the pressure inside the chamber. For the piston type trigger sprayers, as the trigger is compressed, it acts on the fluid in the chamber and the spring, increasing the pressure on the fluid. For the bellows spray dispenser, as the bellows is compressed, the pressure increases on the fluid. The increase in fluid pressure in either trigger spray dispenser acts to open the top outlet check valve. The top valve allows the product to be forced through the swirl chamber and out the nozzle to form a discharge pattern. An adjustable nozzle cap can be used to vary the pattern of the fluid dispensed.

For the piston spray dispenser, as the trigger is released, the spring acts on the piston to return it to its original position. For the bellows spray dispenser, the bellows acts as the spring to return to its original position. This action causes a vacuum in the chamber. The responding fluid acts to close the outlet valve while opening the inlet valve drawing product up to the chamber from the reservoir.

A more complete disclosure of commercially available dispensing devices appears in U.S. Pat. No. 4,082,223, Nozawa, issued Apr. 4, 1978; U.S. Pat. No. 4,161,288, McKinney, issued Jul. 17, 1985; U.S. Pat. No. 4,434,917, Saito et al., issued Mar. 6, 1984; and U.S. Pat. No. 4,819,835, Tasaki, issued Apr. 11, 1989; U.S. Pat. No. 5,303,867, Peterson, issued Apr. 19, 1994; all of said references are incorporated herein by reference.

A broad array of trigger sprayers or finger pump sprayers are suitable for use with the compositions of this invention. These are readily available from suppliers such as Calmar, Inc., City of Industry, Calif.; CSI (Continental Sprayers, Inc.), St. Peters, Mo.; Berry Plastics Corp., Evansville, Ind.—a distributor of Guala® sprayers; or Seaquest Dispensing, Cary, Ill.

The preferred trigger sprayers are the blue inserted Guala® sprayer, available from Berry Plastics Corp., or the Calmar TS800-1A sprayers, available from Calmar Inc., because of the fine uniform spray characteristics, spray volume, and pattern size. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or clear polyethylene terephthalate.

For smaller four fl-oz. size (about 118 ml), a finger pump can be used with canister or cylindrical bottle. The preferred pump for this application is the cylindrical Euromist II®, from Seaquest Dispensing.

III. Method of Use

The composition for reducing malodor impression herein can be used by distributing, e.g., by placing the aqueous solution into a dispensing means, preferably a spray dispenser and spraying an effective amount onto the desired surface or article. An effective amount as defined herein means an amount sufficient to absorb odor to the point that it is not discernible by the human sense of smell yet not so much as to saturate or create a pool of liquid on said article or surface and so that when dry there is no visual deposit readily discernible. Distribution can be achieved by using a spray device, a roller, a pad, etc.

Preferably, the present invention does not encompass distributing the solution on to shiny surfaces including, e.g., chrome, glass, smooth vinyl, leather, shiny plastic, shiny wood, etc. It is preferable not to distribute the solution onto shiny surfaces because spotting and filming can more readily occur on the surfaces. Furthermore, the solution is not for use on human skin, especially when an antimicrobial preservative is present in the composition because skin irritation can occur.

The present invention encompasses the method of spraying an effective amount of the composition for reducing malodor onto household surfaces. Preferably said household surfaces are selected from the group consisting of countertops, cabinets, walls, floors, bathroom surfaces and kitchen surfaces.

The present invention encompasses the method of spraying a mist of an effective amount of the composition for reducing malodor onto fabric and/or fabric articles. Preferably, said fabric and/or fabric articles include, but are not limited to, clothes, curtains, drapes, upholstered furniture, carpeting, bed linens, bath linens, tablecloths, sleeping bags, tents, car interior, e.g., car carpet, fabric car seats, etc.

The present invention encompasses the method of spraying a mist of an effective amount of the composition for reducing malodor impression onto and into shoes wherein said shoes are not sprayed to saturation.

The present invention encompasses the method of spraying a mist of an effective amount of the composition for reducing malodor impression onto shower curtains.

The present invention relates to the method of spraying a mist of an effective amount of the composition for reducing malodor impression onto and/or into garbage cans and/or recycling bins.

The present invention relates to the method of spraying a mist of an effective amount of the composition for reducing malodor impression into the air to absorb malodor.

The present invention relates to the method of spraying a mist of an effective amount of the composition for reducing malodor impression into and/or onto major household appliances including but not limited to: refrigerators, freezers, washing machines, automatic dryers, ovens, microwave ovens, dishwashers etc., to absorb malodor.

The present invention relates to the method of spraying a mist of an effective amount of the composition for reducing malodor impression onto cat litter, pet bedding and pet houses to absorb malodor.

The present invention relates to the method of spraying a mist of an effective amount of the composition for reducing malodor impression onto household pets to absorb malodor.

All percentages, ratios, and parts herein, in the Specification, Examples, and Claims are by weight and are approximations unless otherwise stated.

The following are non-limiting examples of the instant composition. Perfume compositions that are used herein are as follows.

| | A Wt. % | B Wt. % | C Wt. % |
|---|---|---|---|
| Perfume Ingredients | | | |
| 3,7-Dimethyl-6-octenol | 10 | — | 5 |
| Benzyl salicylate | 5 | 20 | 5 |
| Benzyl acetate | 10 | 15 | 5 |
| Benzophenone | 3 | 5 | — |
| Octahydro-3,6,8,8-tetramethyl-1H-3A,7-methanoazulen-6-ol | 2 | — | — |
| 3-Methylene-7-methyl octan-7-ol | 10 | — | 5 |
| Dihydro-nor-cyclopentadienyl acetate | 5 | — | 5 |
| 1,3,4,6,7,8-Hexahydro-4,6,6,7,8,8-hexamethyl-cyclopenta -gamma-2-benzopyrane | 10 | — | — |
| Phenyl ethyl alcohol | 15 | 10 | 20 |
| 3-Hydroxy-3,7-dimethyl-1,6-octadiene acetate | 4 | — | 5 |
| 3-Hydroxy-3,7-dimethyl-1,6-octadiene | 6 | 15 | 5 |
| Methyl dihydro jasmonate | 3 | 10 | 5 |
| 2-Methyl-3(para tert butylphenyl) propionaldehdye | 10 | 15 | 20 |
| Phenyl ethyl acetate | 2 | 5 | 1 |
| 4-Hydroxy-3-methoxybenzaldehyde | — | — | 1 |
| para-Menth-1-en-8-ol, para-menth-1-en-1-ol | 5 | — | 8 |
| Anisic aldehyde | — | — | 2 |
| Coumarin | — | — | 5 |
| 2-Methyl-3-(para iso propylphenyl)propionaldehyde | — | — | 3 |
| Total | 100 | 100 | 100 |

| | D Wt. % | E Wt. % |
|---|---|---|
| Perfume Material | | |
| Amyl salicylate | 8 | — |
| Benzyl acetate | 8 | 8 |
| Benzyl Salicylate | — | 2 |
| Citronellol | 7 | 27 |
| Dihydromyrcenol | 2 | — |
| Eugenol | 4 | — |
| Flor acetate | 8 | — |
| Galaxolide | 1 | — |
| Geraniol | 5 | — |
| Hexyl cinnamic aldehyde | 2 | — |
| Hydroxycitronellal | 3 | — |
| Lilial | 2 | — |
| Linalool | 12 | 13 |
| Linalyl acetate | 5 | — |
| Lyral | 3 | — |
| Methyl dihydrojasmonate | 3 | — |
| Nerol | 2 | — |
| Phenoxy ethyl propionate | — | 3 |
| Phenylethyl acetate | 5 | 17 |
| Phenylethyl alcohol | 8 | 17 |
| alpha-Terpineol | 5 | 13 |
| alpha-Terpinene | 5 | — |
| Tetrahydromyrcenol | 2 | — |
| Total | 100 | 100 |

Perfume D is composed of about 65%, by weight, of ingredients having a Clog P of about 3 or smaller.
Perfume E is composed of about 70%, by weight, of ingredients having a Clog P of about 3 or smaller.

The following are non-limiting examples of the instant composition.

| Ingredients | Example I Wt. % | Example II Wt. % |
|---|---|---|
| Methylated beta-cyclodextrin | 0.2 | — |
| Hydroxypropyl beta-cyclodextrin | — | 0.2 |
| Zinc chloride | 1.0 | 1.0 |
| Perfume A | 0.02 | — |
| Perfume B | — | 0.02 |
| HCl | (a) | (a) |
| Distilled water | Balance | Balance |

(a) To adjust solution pH to about 4.8

EXAMPLES I AND II

The ingredients of Examples I and II are mixed and dissolved into clear solutions.

| Ingredients | Example III Wt. % | Example IV Wt. % |
|---|---|---|
| Methylated alpha-cyclodextrin | 0.1 | — |
| Methylated beta-cyclodextrin | 0.1 | — |
| Hydroxypropyl alpha-cyclodextrin | — | 0.11 |
| Hydroxypropyl beta-cyclodextrin | — | 0.29 |
| Propylene glycol | — | 0.025 |
| Zinc chloride | 2.0 | 1.0 |
| Perfume C | 0.03 | — |
| Perfume D | — | 0.02 |
| HCl | (a) | (a) |
| Distilled water | Balance | Balance |

(a) To adjust solution pH to about 4.8

EXAMPLE III

The ingredients of Example III are mixed and dissolved into clear solutions.

EXAMPLE IV

The ingredients of Example IV are mixed and dissolved into clear solutions. Hydroxypropyl alpha-cyclodextrin and hydroxypropyl beta-cyclodextrin are obtained as a mixture with an average degree of substitution of about 4.9, from the hydroxypolylation reaction of a mixture of alpha-cyclodextrin and beta-cyclodextrin. Propylene glycol is a minor by-product (about 6%) of the same reaction.

| Ingredients | Example V Wt. % | Example VI Wt. % |
|---|---|---|
| Methylated beta-cyclodextrin | 0.5 | — |
| Hydroxypropyl beta-cyclodextrin | — | 0.6 |
| Hydroxypropyl gamma-cyclodextrin | — | 0.3 |
| Zinc chloride | 1.0 | 1.5 |
| Perfume E | 0.1 | — |
| Perfume E | — | 0.15 |
| HCl | (a) | (a) |
| Distilled water | Balance | Balance |

(a) To adjust solution pH to about 4.8

EXAMPLES V AND VI

The ingredients of Examples V and VI are mixed and dissolved into clear solutions. In Example VI, the hydroxypropyl beta-cyclodextrin and hydroxypropyl gamma-cyclodextrin are obtained as a mixture with an average degree of substitution of about 3.8, from the hydroxypolylation reaction of a mixture of beta-cyclodextrin and gamma-cyclodextrin.

| Ingredients | Example VII Wt. % | Example VIII Wt. % |
|---|---|---|
| Methylated beta-cyclodextrin | 0.5 | — |
| Hydroxypropyl-beta-cyclodextrin | — | 0.5 |
| Zinc chloride | 1.0 | 1.0 |
| Perfume E | 0.1 | 0.1 |
| Kathon CG | 0.0008 | 0.0008 |
| HCl | (a) | (a) |
| Distilled water | Balance | Balance |

(a) To adjust solution pH to about 4.8

EXAMPLES VII AND VIII

The ingredients of Examples VII and VIII are mixed and dissolved into clear solutions.

| Ingredients | Example IX Wt. % | Example X Wt. % |
|---|---|---|
| Methylated beta-cyclodextrin | 0.3 | — |
| Hydroxypropyl-beta-cyclodextrin | — | 0.3 |
| Zinc chloride | 1.0 | 1.0 |
| Perfume D | 0.03 | 0.03 |
| Kathon CG | 0.0008 | 0.0008 |
| Surfynol 465[1] | 0.1 | 0.1 |
| HCl | (a) | (a) |
| Distilled water | Balance | Balance |

(a) To adjust solution pH to about 4.8
[1]Surfynol 465 ® available from Air Products, has the general structure:

$$CH_3-CH(CH_3)-CH_2-C(CH_3)(({CH_2CHCO})_5H)-C\equiv C-C(CH_3)(({CH_2CH_2CO})_5H)-CH_2-CH(CH_3)-CH_3$$

EXAMPLES IX AND X

The ingredients of Examples IX and X are mixed and dissolved into clear solutions.

| Ingredients | Example XI Wt. % | Example XII Wt. % |
|---|---|---|
| Methylated beta-cyclodextrin | 0.5 | — |
| Hydroxypropyl beta-cyclodextrin | — | 0.5 |
| $ZnSO_4.7H_2O$ | 2.2 | 2.2 |
| Perfume D | 0.03 | — |
| Perfume E | — | 0.04 |
| Glydant Plus ® | 0.01 | 0.01 |
| Distilled Water | Balance | Balance |

EXAMPLE XI AND XII

The ingredients of Example XI and XII are mixed and dissolved into clear solutions.

EXAMPLES XIII

The composition of Example IV is sprayed onto clothing using a blue inserted Guala® trigger sprayer, available from Berry Plastics Corp. and allowed to evaporate off of the clothing.

EXAMPLE XIV

The composition of Example VII is sprayed onto a kitchen countertop using blue inserted Guala® trigger sprayer, available from Berry Plastics Corp., and wiped off with a paper towel.

EXAMPLE XV

The composition of Example X is sprayed onto clothes using a cylindrical Euromist II® pump sprayer available from Seaquest Dispensing, and allowed to evaporate off of the clothing.

What is claimed:

1. A method of treating an inanimate article or inanimate surface having malodor impression, to reduce said malodor impression, which comprises distributing an effective amount, onto said article or surface, of an aqueous composition for reducing malodor impression, which comprises:

A. from about 0.01% to about 1%, by weight of the composition, of perfume;
   B. aqueous carrier; and wherein said composition is essentially free of any material that would soil or stain fabric; wherein said composition contains from about 1% to less than about 5%, by weight of the composition, of low molecular weight monohydric alcohols; wherein said composition optionally contains only a low level, from about 0.1% to about 5%, of unprotected cyclodextrin or cyclodextrin derivative, all cyclodextrin and cyclodextrin derivatives that are present being solubilized; wherein said composition contains no more than about 3% by weight of the composition of solubilizing agent; and wherein any aerosol propellant that is present is selected from the group consisting of: gaseous hydrocarbons, compressed air, nitrogen, carbon dioxide, and mixtures thereof.

2. The method of claim 1 wherein said perfume is present at a level of from about 0.01% to about 0.5%, by weight of the composition.

3. The method of claim 2 wherein said perfume is present at a level of from about 0.015% to about 0.3%, by weight of the composition.

4. The method of claim 1 wherein at least 25% of the perfume comprises perfume ingredients having a Clog P of about 3 or smaller.

5. The method of claim 4 wherein said perfume ingredients are selected from the group consisting of benzaldehyde, benzyl acetate, cis-3-hexenyl acetate, coumarin, dihydromyrcenol, dimethyl benzyl carbinyl acetate, ethyl vanillin, eucalyptol, eugenol, iso eugenol, flor acetate, geraniol, hydroxycitronellal, linalool, methyl anthranilate, methyl beta naphthyl ketone, methyl dihydro jasmonate, nerol, nonalactone, phenyl ethyl acetate, phenyl ethyl alcohol, alpha terpineol, beta terpineol, vanillin, and mixtures thereof.

6. The method of claim 5 wherein said perfume is present at a level of from about 0.01% to about 0.5%, by weight of the composition.

7. The method of claim 6 wherein said perfume is present at a level of from about 0.015% to about 0.3%, by weight of the composition.

8. The method of claim 1 additionally comprising from about 0.1% to about 5%, by weight of the composition, of solubilized, water-soluble, uncomplexed cyclodextrin and wherein the perfume to cyclodextrin weight ratio is from about 3:100 to about 100:100.

9. The method of claim 8 wherein the water-soluble cyclodextrin is selected from the group consisting of derivatised beta-cyclodextrins, alpha-cyclodextrin and its derivatives, gamma-cyclodextrin and its derivatives, and mixtures thereof.

10. The method of claim 9 wherein the cyclodextrin derivatives are selected from the group consisting of methyl substituted cyclodextrins, ethyl substituted cyclodextrins, hydroxyalkyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, and mixtures thereof.

11. The method of claim 10 wherein said cyclodextrin is selected from the group consisting of alpha-cyclodextrin, methylated alpha-cyclodextrin, methylated beta-cyclodextrin, hydroxyethyl alpha-cyclodextrin, hydroxyethyl beta-cyclodextrin, hydroxypropyl-alpha-cyclodextrin, hydroxypropyl-beta-cyclodextrin, and mixtures thereof.

12. The method of claim 8 wherein said cyclodextrin is present at a level of from about 0.2% to about 4%, by weight of the composition and wherein the weight ratio of perfume to cyclodextrin is from about 4:100 to about 50:100.

13. The method of claim 12 wherein said cyclodextrin is present at a level of from about 0.3% to about 3%, by weight of the composition and wherein the weight ratio of perfume to cyclodextrin is from about 5:100 to about 25:100.

14. The method of claim 1 wherein said composition additionally comprises water-soluble metallic salt selected from the group consisting of water-soluble zinc salts, water-soluble copper salts, and mixtures thereof, present at a level of from about 0.1% to about 10%, by weight of the composition.

15. The method of claim 14 wherein said metallic salt is selected from the group consisting of zinc chloride, zinc gluconate, zinc lactate, zinc maleate, zinc salicylate, zinc sulfate, copper chloride, copper gluconate, and mixtures thereof.

16. The method of claim 15 wherein said metallic salt is $ZnCl_2$ present at a level of from about 0.2% to about 7%, by weight of the composition.

17. The method of claim 1 wherein said composition additionally comprises a solubilizing agent.

18. The method of claim 17 wherein said solubilizing agent is a low foaming surfactant selected from the group consisting of nonionic surfactants, cationic surfactants, amphoteric surfactants, zwitterionic surfactants, and mixtures thereof present at a level of from about 0.05% to about 1%, by weight of the composition.

19. The method of claim 1 wherein said composition additionally comprises an effective amount of a water-soluble, antimicrobial preservative having a water-solubility of greater than about 0.3%, by weight at room temperature.

20. The method of claim 1, which comprises spraying a mist of an effective amount of said composition for reducing malodor impression onto fabric, wherein said fabric is not sprayed to saturation.

21. The method of claim 20 wherein said fabric is selected from the group consisting of clothes, curtains, drapes, upholstered furniture, carpets, bed linens, bath linens, tents, sleeping bags, car carpeting and fabric car seats.

22. The method of claim 1, which comprises spraying a mist of an effective amount of the composition for reducing malodor impression onto household surfaces.

23. The method of claim 22 wherein said household surface is selected from the group consisting of countertops, cabinets, walls, floors, bathroom surfaces, and kitchen surfaces.

24. The method of claim 1, which comprises spraying a mist of an effective amount of the composition for reducing malodor impression onto and into shoes, wherein said shoes are not sprayed to saturation.

25. The method of claim 1, which comprises spraying a mist of an effective amount of the composition for reducing malodor impression onto and into garbage cans and recycling bins.

26. The method of claim 1, which comprises spraying a mist of an effective amount of the composition for reducing malodor impression into and onto major household appliances.

27. The method of claim 1, which comprises spraying a mist of an effective amount of the composition for reducing malodor impression onto cat litter.

28. The method of claim 1, which comprises spraying a mist of an effective amount of the composition for reducing malodor impression onto household pet beds.

29. A method of treating fabrics, which comprises spraying onto fabrics an effective amount of a mist of the composition for reducing malodor impression comprising from about 0.015% to about 0.3%, by weight of the composition of perfume wherein at least 25% of the perfume ingredients have a Clog P of 3 or smaller and water; and wherein said composition is essentially free of any material that would soil or stain fabric and wherein said composition contains less than 1%, by weight of the composition of low molecular weight monohydric alcohols; optionally, less than about 3% surfactant by weight of the composition; and optionally contains only a low level, from about 0.1% to about 5%, of unprotected cyclodextrin or cyclodextrin derivative, all cyclodextrin and cyclodextrin derivatives that are present being solubilized.

30. A method of treating household surfaces which comprises spraying a mist, with a trigger-spray dispenser having a bottle comprising clear polyethyleneterephthalate, of an effective amount onto said household surfaces, of the composition for reducing malodor impression comprising, from about 0.015% to about 0.3%, by weight of the composition, of perfume wherein at least 25% of the perfume ingredients have a Clog P of 3 or less; from about 0.1% to about 5%, by weight of the composition, of hydroxypropyl beta-cyclodextrin, wherein the perfume to cyclodextrin weight ratio is from about 3:100 to about 100:100; from about 0.1% to about 10%, by weight of the composition of $ZnCl_2$; from about 0.5% to about 1%, by weight of the composition, of low-foaming surfactant; and from about 0.0001% to about 0.5%, by weight of the composition, of a solubilized, water-soluble antimicrobial preservative comprising a mixture of 5-chloro-2-methyl-4-isothiazolin-3-one and 2-methyl-4-isothiazolin-3-one; and water, wherein said composition is essentially free of any material that would soil or stain fabric and wherein said composition contains less than 3%, by weight of the composition of low molecular weight monohydric alcohols.

31. The method of claim 30 wherein said composition comprises from about 0.1% to about 5% of said cyclodextrin and wherein the perfume to cyclodextrin weight ratio is from about 5:100 to about 100:100.

32. The method of claim 30 wherein said composition comprises said $ZnCl_2$ present at a level of from about 0.3% to about 5% by weight of the composition.

33. A method of treating an inanimate object or inanimate surface which has malodor impression to reduce said malodor impression which comprises spraying an effective amount onto said inanimate object or inanimate surface, of composition for reducing malodor impression consisting essentially of: from about 0.015% to about 1% by weight of the composition of perfume; optionally, from about 0.1% to about 5% by weight of the composition of hydroxypropyl beta-cyclodextrin, wherein the perfume to cyclodextrin weight ratio is from about 5:100 to about 25:100; optionally, from about 0.3% to about 5%, by weight of the composition of $ZnCl_2$; optionally, from about 0.05% to about 1%, by weight of the composition, of surfactant; optionally, from about 0.0001% to about 0.5%, by weight of the composition, of solubilized, water-soluble antimicrobial preservative; and the balance of the composition consisting essentially of a mixture of water and from about 1% to less than about 5% by weight of the composition, of low molecular weight monohydric alcohol, and wherein said composition is essentially free of any material that would soil or stain fabric; and wherein any aerosol propellant that is present is selected from the group consisting of: gaseous hydrocarbons, compressed air, nitrogen, carbon dioxide, and mixtures thereof.

34. The method of claim 33 wherein said composition contains from about 0.1% to about 1%, by weight of the composition, of surfactant.

35. A method of treating an inanimate object having malodor impression to reduce said malodor impression which comprises spraying an effective amount onto said inanimate object, of composition for reducing malodor impression consisting essentially of: from about 0.015% to about 1% by weight of the composition of perfume; optionally, from about 0.1% to about 5% by weight of the composition of solubilized, unprotected cyclodextrin; optionally, from about 0.05% to about 1%, by weight of the composition, of surfactant; optionally, from about 0.001% to about 0.5%, by weight of the composition, of solubilized, water-soluble antimicrobial preservative; and the balance being an aqueous carrier consisting essentially of water and from about 1% to less than about 5% by weight of the composition, of low molecular weight monohydric alcohol, and wherein said composition is essentially free of any material that would soil or stain fabric.

36. The method of claim 35 wherein the level of cyclodextrin in said composition is 0%.

37. A method of treating an inanimate object or inanimate surface which has malodor impression to reduce said malodor impression which comprises spraying an effective amount onto said inanimate object or inanimate surface, of composition for reducing malodor impression consisting essentially of: from about 0.015% to about 1% by weight of the composition of perfume; optionally, from about 0.1% to about 10% by weight of the composition of water soluble metallic salt selected from the group consisting of water soluble zinc salts, water soluble copper salts, and mixtures thereof; optionally, from about 0.05% to about 1%, by weight of the composition, of surfactant; optionally, from about 0.0001% to about 0.5%, by weight of the composition, of solubilized, water-soluble antimicrobial preservative; and the balance being an aqueous carrier consisting essentially of water and from about 1% to less than about 5% by weight of the composition, of low molecular weight monohydric alcohol, and wherein said composition is essentially free of any material that would soil or stain fabric; and wherein any aerosol propellant that is present is selected from the group consisting of: gaseous hydrocarbons, compressed air, nitrogen, carbon dioxide, and mixtures thereof.

38. A method of treating an inanimate object or inanimate surface which has malodor impression to reduce said malodor impression which comprises spraying an effective amount onto said inanimate object or inanimate surface, of composition for reducing malodor impression consisting essentially of: from about 0.015% to about 1% by weight of the composition of perfume; optionally, an effective amount to improve the control of odor of material selected from the group consisting of solubilized, unprotected cyclodextrin, metallic salt, and mixtures thereof; optionally, from about 0.05% to about 1%, by weight of the composition, of surfactant; optionally, from about 0.0001% to about 0.5%, by weight of the composition, of solubilized, water-soluble antimicrobial preservative; and the balance being an aqueous carrier consisting essentially of water and from about 1% to less than about 5% by weight of the composition, of low molecular weight monohydric alcohol, and wherein said composition is essentially free of any material that would soil or stain fabric; and wherein any aerosol propellant that is present is selected from the group consisting of; gaseous hydrocarbons, compressed air, nitrogen, carbon dioxide, and mixtures thereof.

39. A method of treating an inanimate object or inanimate surface which has malodor impression to reduce said malodor impression which comprises spraying an effective amount onto said inanimate object or inanimate surface, of composition for reducing malodor impression consisting essentially of: from about 0.015% to about 1% by weight of the composition of perfume; optionally, an effective amount of additional ingredient for reducing malodor, selected from the group consisting of: (a) from about 0.1% to about 2%, by weight of the composition, of solubilized, unprotected cyclodextrin; (b) from about 0.1% to about 5% by weight of the composition of water soluble metallic salt selected from the group consisting of water soluble zinc salts, water soluble copper salts, and mixtures thereof; and (c) mixtures thereof; optionally, from about 0.05% to about 1%, by weight of the composition, of surfactant; optionally, from about 0.0001% to about 0.5%, by weight of the composition, of solubilized, water-soluble antimicrobial preservative; and the balance being an aqueous carrier consisting essentially of water and from about 1% to less than about 5% by weight of the composition, of low molecular weight monohydric alcohol, and wherein said composition is essentially free of any material that would soil or stain fabric; and wherein any aerosol propellant that is present is selected from the group consisting of: gaseous hydrocarbons, compressed air, nitrogen, carbon dioxide, and mixtures thereof.

40. The method of claim 39 wherein the composition contains surfactant.

41. The method of claim 40 wherein said surfactant is low-foaming surfactant selected from the group consisting of nonionic surfactants, cationic surfactants, amphoteric surfactants, zwitterionic surfactants, and mixtures thereof present at a level of from about 0.02% to about 1%, by weight of the composition.

* * * * *